United States Patent [19]

Miyazaki

[11] Patent Number: 4,676,230
[45] Date of Patent: Jun. 30, 1987

[54] ENDOSCOPE APPARATUS WITH A REMOVABLE INSERTION GUIDE

[75] Inventor: Atsushi Miyazaki, Tokyo, Japan
[73] Assignee: Olympus Optical Co., Ltd., Tokyo, Japan
[21] Appl. No.: 823,416
[22] Filed: Jan. 28, 1986

[30] Foreign Application Priority Data

Feb. 8, 1985 [JP] Japan .................. 60-22963

[51] Int. Cl.⁴ ........................................ A61B 1/00
[52] U.S. Cl. ........................................... 128/4
[58] Field of Search ............................ 128/4–8; 73/151

[56] References Cited

U.S. PATENT DOCUMENTS

| | | | |
|---|---|---|---|
| 1,959,127 | 5/1934 | Duerme | 128/6 |
| 3,677,262 | 7/1972 | Zukowski | 128/6 |
| 4,306,546 | 12/1981 | Heine et al. | 128/6 |
| 4,491,865 | 1/1985 | Danne et al. | 128/4 |
| 4,494,549 | 1/1985 | Namba et al. | 128/4 |
| 4,517,962 | 5/1985 | Heckele | 128/6 |
| 4,577,621 | 3/1986 | Patel | 128/4 |

FOREIGN PATENT DOCUMENTS

| | | | |
|---|---|---|---|
| 3111412 | 11/1982 | Fed. Rep. of Germany | 128/4 |
| 2249641 | 5/1975 | France | 128/7 |
| 56135820 | 10/1980 | Japan . | |

*Primary Examiner*—Kyle L. Howell
*Assistant Examiner*—Max F. Hindenburg

[57] ABSTRACT

An endoscope apparatus includes an insertion section to be inserted into a desired object of inspection, and a substantially cylindrical insertion guide for assisting insertion of the insertion section into the object. A threaded portion and an engaging portion are formed around the distal end portion of the insertion section. The guide has a guide body removably fitted around the distal end portion of the insertion section. The body has a threaded portion engaged with the threaded portion of the insertion section and a plurality of jugs which are pressed inward by a cylindrical cover fitted around the body to engage the engaging portion, thereby preventing the body from moving.

6 Claims, 7 Drawing Figures

ENDOSCOPE APPARATUS WITH A REMOVABLE INSERTION GUIDE

BACKGROUND OF THE INVENTION

The present invention relates to an endoscope apparatus, and more specifically to an endoscope apparatus with an insertion guide for assisting insertion of an insertion section of an endoscope into an object of inspection.

Endoscopes, especially industrial endoscopes, are used for the observation of various objects of inspection of different sizes. However, when inserting an insertion section of one such conventional endoscope into a duct with an inner diameter greater than the outer diameter of the distal end portion of the section, for example, the insertion section would stagger in the duct, failing to accurately fix the viewing direction. Moreover, the insertion section would be biased to the bottom side of the duct, thus permitting observation of only the bottom wall portion of the duct.

Thereupon, an endoscope with an insertion guide is disclosed in, e.g., Japanese Patent Disclosure No. 135820/81. The guide is mounted around the distal end portion of the insertion section, and assists it in being inserted into the object of inspection. The guide is fitted on the insertion section by screwing a threaded portion formed on the outer peripheral surface of the distal end portion of the section into another threaded portion formed on the inner peripheral surface of the guide, or by pressure-bonding part of the guide to part of the insertion section.

According to the screwing method, however, the engagement between the two threaded portions may become loose during use, so that the insertion guide may become disengaged from the insertion section. In the case of the bonding method, on the other hand, the guide requires a complicated clamping mechanism.

SUMMARY OF THE INVENTION

The present invention is contrived in consideration of these circumstances, and is intended to provide an endoscope apparatus, simple in construction and capable of securely preventing an insertion guide from slipping off an insertion section of an endoscope.

In order to achieve the above object, an endoscope apparatus according to the present invention comprises an operation section, an insertion section extending from the operation section and adapted to be inserted into a desired object of inspection, the insertion section including a threaded portion formed around the distal end portion thereof and an engaging portion formed around that portion of the insertion section which is nearer to the proximal end thereof than the threaded portion, and a substantially cylindrical insertion guide removably mounted around the distal end portion of the insertion section, for assisting insertion of the insertion section into the object of inspection, the guide including a guide-side threaded portion formed on the inner peripheral surface thereof and adapted to engage the threaded portion of the insertion section, and retaining means for engage the engaging portion to prevent the guide from moving.

BRIEF DESCRIPTION OF THE DRAWINGS

FIGS. 1 to 3 show an endoscope apparatus according to an embodiment of the present invention, in which FIG. 1 is a general perspective view of the apparatus, FIG. 2 is a side view of a distal end portion of an insertion section, and FIG. 3 is a sectional view of an insertion guide;

FIGS. 4 to 6 show a modification of the insertion guide, in which FIG. 4 is a cutaway side view of the insertion guide, FIG. 5 is a sectional view taken along line V—V of FIG. 4, and FIG. 6 is a sectional view taken along line VI—VI of FIG. 4.

DETAILED DESCRIPTION OF THE PREFERRED EMBODIMENT

An embodiment of the present invention will now be described in detail with reference to the accompanying drawings.

Figure 1:
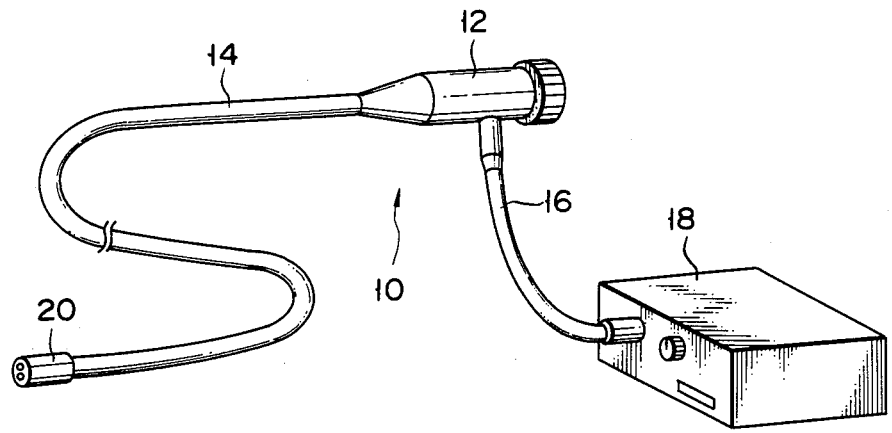

As shown in FIG. 1, an endoscope apparatus has endoscope body 10. Body 10 includes operation section 12, flexible insertion section 14, and light guide cable 16. Section 14 and cable 16 both extend from section 12. The extended end of cable 16 is connected to light source unit 18.

Figure 2:
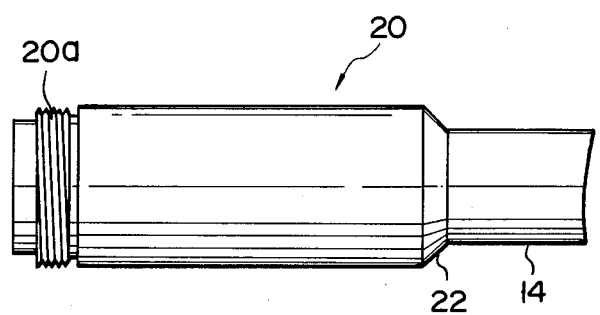

As shown in FIG. 2, distal end structure 20 is attached to the distal end of insertion section 14. Structure 20 is greater in diameter than section 14. Tapered step portion 22 comprises an engaging position and is formed at the rear end of structure 20. External threaded portion 20a is formed around the distal end of structure 20.

Figure 3:
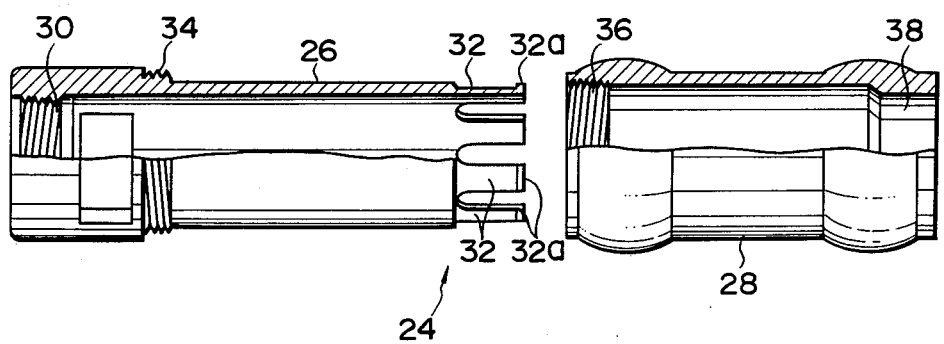

The endoscope apparatus is provided with insertion guide 24 which is fitted on distal end structure 20. As shown in FIG. 3, guide 24 includes substantially cylindrical guide body 26 fitted on structure 20 and substantially cylindrical cover 28 comprising a pressure member fitted on body 26. Body 26 has internal threaded portion 30 formed on the inner peripheral surface of one end portion thereof. Portion 30 is adapted to engage threaded portion 20a of structure 20. A plurality of slits are cut in the other end portion of body 26 so that a plurality of cantilevershaped lugs 32 comprising retaining means are arranged at regular intervals around the circumference of body 26. Projection 32a is formed on the extended end of each lug 32, projecting radially outward. External threaded portion 34 is formed on the outer peripheral surface of the middle portion of body 26.

Guide body 26 is fitted on distal end structure 20 from the distal end side of insertion section 14 so that threaded portion 30 can be screwed in threaded portion 20a of structure 20. Thus, body 26 is removably fitted around structure 20. When body 26 is on structure 20, lugs 32 of body 26 are located outside step portion 22.

Cover 28 has internal threaded portion 36 formed on the inner peripheral surface of one end portion thereof and adapted to engage threaded portion 34 of guide body 26. Short-diameter portion 38 to engage lugs 32 of body 26 is formed at the other end of cover 28. The inner diameter of portion 38 is shorter than the diameter of an imaginally circle which is described around the tips of projections 32a on lugs 32.

First, cover 28 is mounted on distal end structure 20 and is pulled backward along insertion section 14 toward operation section 12.

After, guide body 26 is mounted on distal end structure 20 so as to be engaged with treaded portion 20a. Then cover 28 is then moved back toward distal end structure 20 to be is fitted around body 26 so that threaded portion 36 engages threaded portion 34 of body 26. Thus, cover 28 is removably mounted on body 26. When cover 28 is on body 26, the inner peripheral surface of short-diameter portion 38 of cover 28 presses projections 32a of lugs 32 inward, so that the tip portions of lugs 32 are constricted to firmly engage step portion 22 of structure 20.

When inserting insertion section 14 of endoscope body 10 into a duct or the like whose inner diameter is greater than the outer diameter of distal end structure 20, insertion guide 24 is mounted on structure 20. Cover 28 used in this case has an outer diameter substantially equal to the inner diameter of the duct. If section 14 is inserted into the duct with guide 24 on structure 20, structure 20 moves in a manner such that the outer surface of cover 28 is in contact with the inner surface of the duct. Thus, structure 20 is prevented from staggering in the duct or from being biased to the bottom side of the duct.

If several covers with different diameters are prepared, the endoscope apparatus may be applied to various objects of inspection with different inner diameters by using the different sized covers.

According to the endoscope apparatus constructed in this manner, insertion guide 24 is mounted on distal end structure 20 of endoscope body 10 so that guide body 26 is screwed and held on distal end structure 20. Also, lugs 32 of body 26 are constricted by cover 28 and thus body 26 is prevented from loosening. If the engagement between threaded portions 30 and 20a of body 26 and structure 20 becomes loose to allow body 26 to advance, the tip portions of lugs 32 constricted by short-diameter portion 38 of cover 28 engage step portion 22 of structure 20. Accordingly, body 26 is prevented from moving or slipping off structure 20. This indicates that the insertion guide, during inspection, can securely be prevented from dropping into the object of inspection. Thus, it is impossible that the object would ever have to be dismantled to remove the guide therefrom. The secure retention of the guide can be effected by means of only a simple arrangement including projecting portions formed on the guide engaging a step portion on the distal end portion of the endoscope.

Figure 4:
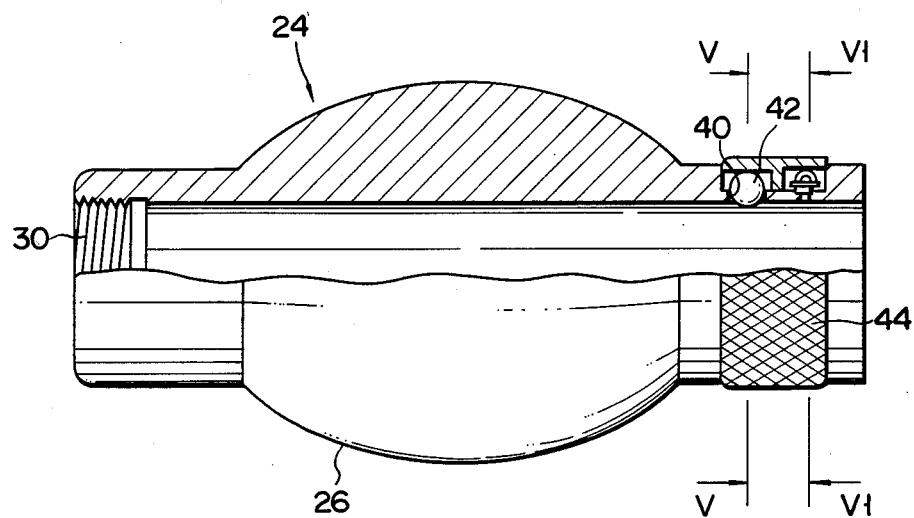
Figure 5:
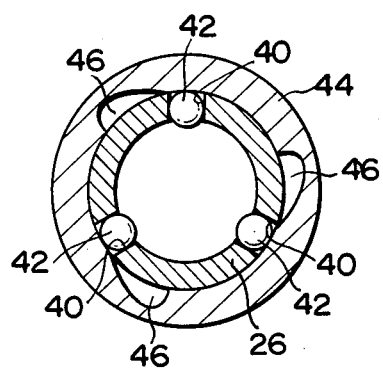
Figure 6:
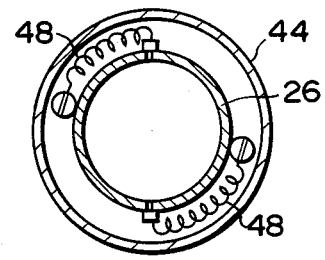

FIGS. 4 to 6 show a modification of the insertion guide. Substantially cylindrical in shape although guide body 26 bulges in the middle. Formed on the inner peripheral surface of one end portion of body 26 is internal threaded portion 30 which engages threaded portion 20a of distal end structure 20. As shown in FIGS. 4 and 5, three through holes 40 are formed in the other end portion of body 26, spaced circumferentially at regular intervals. Retaining balls 42 comprising retaining means are fitted individually in through holes 40 so as to project into the bore of body 26. Operating ring 44 comprisng a pressure member is rotatably mounted around the other end portion of body 26, facing through holes 40. Three ball escape grooves 46 are formed in the inner peripheral surface of operating ring 44, arranged circumferentially at regular intervals. If ring 44 is rotated to a position where grooves 46 face balls 42, the balls escape into the grooves to retract from the inner peripheral surface of body 26. If ring 44 is rotated so that escape grooves 46 are deviated from holes 40, balls 42 are pressed by the inner peripheral surface of ring 44 to project into the bore of body 26.

As shown in FIG. 6, a pair of springs 48 are arranged between operating ring 44 and body 26. Springs 48 urge ring 44 toward the position where escape grooves 46 deviate from through holes 40, thereby pressing balls 42 inward. When insertion guide 24 is mounted on distal end structure 20 of the endoscope, balls 42 engage step portion 22 to prevent guide 24 from slipping off structure 20.

In mounting insertion guide 24 with the aforementioned construction on distal end structure 20, operating ring 44 is first rotated, against the urging force of springs 48, to the position where escape grooves 46 face through holes 40. Then, structure 20 is inserted into body 26 from the other end side thereof. As a result, balls 42 escape into grooves 46, pressed by the outer peripheral surface of structure 20. Body 26 is then fixed on structure 20 by engaging threaded portions 30 and 20a with each other. Thereafter, if ring 44 is released, it is rotated by the urging force of springs 48 causing balls 42 to project. Thus, balls 42 engage step portion 22 of structure 20, thereby preventing body 26 from slipping off structure 20.

Insertion guide 24 can be removed from distal end structure 20 by following the aforesaid steps in the opposite order.

The modified insertion guide constructed in this manner, like the one according to the foregoing embodiment, can securely be prevented from coming off the distal end structure despite the simple design.

In the above modification, moreover, the retaining balls may be varied in number as required.

Figure 7:
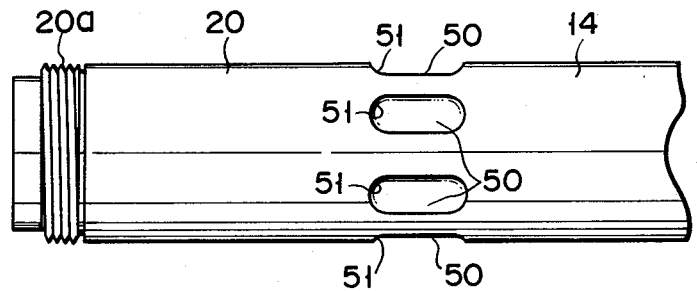
FIG. 7 is a side view showing a modification of the distal end portion of the insertion section.

FIG. 7 shows a modification of the distal end structure. According to this modification, structure 20 is formed with a plurality of grooves 50 in place of the step portion. Grooves 50, which correspond in number to lugs 32 or retaining balls 42, each extend in the axial direction of structure 20. The distal-side end face of each groove 50 defines stop portion 51.

According to this modification, when insertion guide 24 is mounted on distal end structure 20, lugs 32 or retaining balls 42 engage grooves 50 to prevent guide 24 from rotating. Thus, the guide is securely prevented from coming off the distal end structure.

What is claimed is:

1. An endoscope apparatus comprising:
   an operation section;
   an insertion section extending from the operation section for insertion into a desired object of inspection, a distal end portion and a proximal end to the operation section on said insertion section; said insertion section including a threaded portion formed around the distal end portion thereof, and an engaging portion formed on that portion of the outer periphery of the insertion section which is nearer to the proximal end thereof than the threaded portion; and
   a substantially cylindrical insertion guide removably mounted on the outer peripheral surface of the distal end portion of the insertion section for assisting insertion of the insertion section into the object of inspection, said guide including a guide-side threaded portion formed on an inner peripheral surface thereof and adapted to engage the threaded portion of the insertion section, and retaining means for engaging the engaging portion to prevent the guide from moving, said retaining means including a plurality of projecting portions capable of projecting into a bore of the guide, and a pressure member provided outside the projecting portions for pressing the projecting portions to engage the engaging portion of the insertion section.

2. The endoscope apparatus according to claim 1, wherein said projecting portions include a plurality of cantilever-shaped lugs projecting from one end portion of the guide and capable of elastic deformation, said lugs being arranged at regular intervals in the circumferential direction of the guide, and said pressure member includes a cylindrical cover fitted around the guide and having a short-diameter portion with an inner diameter shorter than the outer diameter of the guide, for pressing the lugs inward.

3. The endoscope apparatus according to claim 1, wherein said guide has a plurality of through holes formed at regular intervals in the circumferential direction thereof, said projecting portions include a plurality of retaining balls movably fitted in the through holes to project into the bore of the guide, and said pressure member includes an operating ring rotatably disposed around the guide to face the through holes, said operating ring having an inner peripheral surface for pressing the retaining balls into the bore of the guide and a plurality of ball escape grooves formed in the inner peripheral surface at regular intervals, so that retaining balls escape into the escape grooves when the operating ring is rotated to a position where the grooves face the through holes.

4. The endoscope apparatus according to claim 3, wherein said retaining means includes an urging member for urging the operating ring toward a position where the ball escape grooves deviate from the through holes.

5. The endoscope apparatus according to claim 1, wherein said engaging portion includes a ring-shaped step portion formed around the distal end portion of the insertion section.

6. The endoscope apparatus according to claim 1, wherein said engaging portion includes a plurality of grooves formed in the outer peripheral surface of the distal end portion of the insertion section, arranged circumferentially at regular intervals.

* * * * *